(12) United States Patent
Murai

(10) Patent No.: US 10,472,590 B2
(45) Date of Patent: Nov. 12, 2019

(54) DRY-MODE OIL/FAT SEPARATION METHOD

(71) Applicant: FUJI OIL HOLDINGS INC., Osaka (JP)

(72) Inventor: Kenji Murai, Osaka (JP)

(73) Assignee: FUJI OIL HOLDINGS INC., Osaka (JP)

( * ) Notice: Subject to any disclaimer, the term of this patent is extended or adjusted under 35 U.S.C. 154(b) by 0 days.

(21) Appl. No.: 16/462,541

(22) PCT Filed: Nov. 21, 2017

(86) PCT No.: PCT/JP2017/041759
§ 371 (c)(1),
(2) Date: May 21, 2019

(87) PCT Pub. No.: WO2018/097118
PCT Pub. Date: May 31, 2018

(65) Prior Publication Data
US 2019/0276768 A1    Sep. 12, 2019

(30) Foreign Application Priority Data
Nov. 28, 2016    (JP) ................................ 2016-230442

(51) Int. Cl.
*C11B 7/00*    (2006.01)
*B01D 9/00*    (2006.01)

(52) U.S. Cl.
CPC .......... *C11B 7/0083* (2013.01); *B01D 9/0036* (2013.01); *C07B 2200/13* (2013.01)

(58) Field of Classification Search
CPC .. C11B 7/0083; B01D 9/0036; C07B 2200/13
USPC ........................................................ 554/211
See application file for complete search history.

(56) References Cited

FOREIGN PATENT DOCUMENTS

| JP | S5477605 | 6/1979 | |
|---|---|---|---|
| JP | 2005281462 | 10/2005 | |
| JP | 2010285275 | 12/2010 | |
| JP | 2012188584 | 10/2012 | |
| JP | 2012188584 A | * 10/2012 | |
| JP | 2013053187 | 3/2013 | |
| JP | 2013053187 A | * 3/2013 | |
| JP | 2016077175 | 5/2016 | |
| JP | 2016077175 A | * 5/2016 | |
| WO | 2010089973 | 8/2010 | |
| WO | WO-2010089973 A1 | * 8/2010 | ........... C11B 7/0083 |

OTHER PUBLICATIONS

"International Search Report (Form PCT/ISA/210) of PCT/JP2017/041759," dated Jan. 16, 2018, with English translation thereof, pp. 1-4.

* cited by examiner

*Primary Examiner* — Deborah D Carr
(74) *Attorney, Agent, or Firm* — JCIPRNET

(57) ABSTRACT

The present invention addresses the problem of providing a crystallization method having excellent separation performance between a crystal fraction and a liquid fraction after crystallization in a dry-mode separation method employing stirring crystallization and compression filtration, whereby it becomes possible to produce an SUS-rich oil/fat from an SUS-containing oil/fat. In the dry-mode oil/fat separation for producing an SUS-rich oil/fat having an SUS content of 60% by weight or more from an SUS-containing oil/fat having an SUS content of 30% by weight or more, a crystalline S3 component is added to the SUS-containing oil/fat in an amount of 5 to 200 ppm by weight relative to the amount of the SUS-containing oil/fat at a temperature that is higher by 0 to 2° C. than a cloud point of the SUS-containing oil/fat so as to be mixed, and performing stirring crystallization.

6 Claims, No Drawings

DRY-MODE OIL/FAT SEPARATION METHOD

CROSS-REFERENCE TO RELATED APPLICATION

This application is a 371 application of the International PCT application serial no. PCT/JP2017/041759, filed on Nov. 21, 2017, which claims the priority benefit of Japan Patent Application No. 2016-230442, filed on Nov. 28, 2016. The entirety of each of the abovementioned patent applications is hereby incorporated by reference herein and made a part of this specification.

TECHNICAL FIELD

The present invention relates to dry-mode oil/fat separation, and more particularly relates to a method for adding and mixing a specific seed agent during a crystallization step, performing stirring crystallization thereafter, and then separating a crystal fraction and a liquid fraction through compression filtration in dry-mode oil/fat separation.

BACKGROUND ART

Natural oils/fats, mixtures of natural oils/fats, hydrogenated oils and transesterified oils thereof are mixtures of various triglycerides having different melting points. An oil/fat is used for wide range of applications such as frying oil/fat, margarine/shortening oil/fat, filling oil/fat, and chocolate oil/fat, and the like depending on physical properties thereof. Separation of oil/fat such as dry-mode oil/fat separation and solvent separation has been widely put into practical use as one of the processing techniques for adjusting physical properties of oils/fats.

The above-mentioned solvent separation has been suitably used since early times for fractionation of a crystal fraction and a liquid fraction, but a large amount of hexane or acetone, which is an organic solvent, is required. Accordingly, in recent years, a dry-mode oil/fat separation method which is simpler and safer has been extensively studied from the viewpoint of safety and security.

A dry-mode oil/fat separation method is a method in which, in general, a raw material oil/fat completely melted by heating without using a solvent is cooled in a crystallization tank while stirring to precipitate (crystallize) a crystal, and then the precipitate is fractionated into a crystal fraction and a filtrate (unsolidified low-melting-point fraction) by compression and filtration. The method has already been widely used for separating palm kernel oil, butter oil, and palm oil.

The dry-mode oil/fat separation method is more preferable than solvent separation also in terms of energy efficiency. However, there are problems such as solid-liquid separability between a crystal fraction and a liquid fraction is low when compared with solvent separation, removing a liquid fraction entrapped by a crystal fraction is not easy, and when an amount of crystals after crystallization is too large, a viscosity of a crystal slurry increases, and therefore separation by compression and filtration becomes difficult to perform.

CITATION LIST

Patent Literature

In order to solve the above problems, various crystal modification methods have been proposed. Patent Literature 1 relates to a natural separation method in which, in separation of an oil/fat containing high-melting-point components, an oil/fat in a molten state is cooled to a temperature 0 to 30° C. higher than a rising melting point, thereafter, seed crystals of high-melting-point components are inoculated, followed by cooling to a separation temperature, and precipitating the high-melting-point components. According to this method, it is possible to separate high-melting-point components with good yield and good filterability, and to greatly shorten a crystallization time required for crystallization of the high-melting-point components. However, there was a problem of taking a considerably long time to prepare a slurry containing a chestnut bur-like 13 crystal as a seed crystal of high-melting-point components.

Patent Literature 2 relates to a seed separation method of oil/fat, particularly to a method for separating oil/fat by a seed subjected to high pressure treatment, which is a method utilizing a seed prepared by applying a high pressure of 10 to 400 MPa to oil/fat containing a plurality of oil/fat components of different compositions. According to this method, it is possible to shorten a seed preparation time, shorten a crystallization time, and improve filtration performance; however, there is a problem of the method being inefficient because a special device for high pressure treatment was required.

Patent Literature 3 relates to a dry separation method for increasing a crystallization rate by adding a free fatty acid having 4 to 14 carbon atoms into a raw material oil/fat, which is a method capable of performing efficient dry separation at an increased crystallization rate while maintaining the purity of a crystal high. This method is one of the effective dry separation methods. However, because a free fatty acid is concentrated in a low-melting-point fraction after separation, the method is disadvantageous in that a purification load of the low-melting point-fraction becomes extremely large.

[Patent Literature 1]
  Japanese Patent Laid-open No. S54-77605
[Patent Literature 2]
  Japanese Patent Laid-open No. 2005-281462
[Patent Literature 3]
  Japanese Patent Laid-open No. 2012-188584

SUMMARY OF INVENTION

Technical Problem

An object of the present invention is to provide a crystallization method having excellent separability between a crystal fraction and a liquid fraction after crystallization in a dry-mode oil/fat separation method employing stirring crystallization and compression filtration of an oil/fat.

Solution to Problem

In previously filed Japanese Patent Application No. 2010-285275, the applicant of the present invention has completed a separation method in which a specific amount of an auxiliary filtering agent is added to and mixed with a raw material oil/fat before crystallization or a crystal slurry after completion of crystallization, and then compression or filtration is performed, and therefore excellent solid-liquid separability is obtained. However, the applicant of the present invention has made continued efforts to reduce production equipment costs and production costs. Under such a circumstance, as a result of further intensive research on a method for solving problems of thickening of a crystal slurry in the stirring crystallization method, on a method for reducing an amount of filtrate entrapped by crystals, and the like, the applicant of the present invention has found a method in which, by adding a specific seed agent during a crystallization step, it is possible to easily improve solid-liquid separation performance after crystallization, and to obtain a crystal fraction enriched in SUS at a higher yield, and therefore has completed the present invention.

That is, a first aspect of the present invention is a crystallization method, including adding a crystalline S3 component to an SUS-containing oil/fat at 5 to 200 ppm by weight with respect to an amount of the SUS-containing oil/fat at a temperature that is 0 to 2° C. higher than a cloud point of the SUS-containing oil/fat so as to be mixed, and performing stirring crystallization, in dry-mode oil/fat separation for obtaining an SUS-rich oil/fat having an SUS content of 60% by weight or more from the SUS-containing oil/fat having an SUS content of 30% by weight or more by employing stirring crystallization and compression filtration.

(SUS: 1,3-di-saturated-2-unsaturated glyceride, S3: tri-saturated triglyceride, S: saturated fatty acid having 16 to 22 carbon atoms, U: unsaturated fatty acid having 18 carbon atoms)

In a second aspect according to the crystallization method of the first aspect, a crystalline amount of a crystal slurry subjected to the compression filtration is 10 to 20% by weight as a solid fat content.

In a third aspect according to the crystallization method of the second aspect, the SUS is StOSt (St: stearic acid, O: oleic acid).

In a fourth aspect according to the crystallization method of the third aspect, the S3 component is a tri-saturated triglyceride derived from an extremely hydrogenated oil of an oil/fat that is in a liquid form at room temperature.

In a fifth aspect according to the crystallization method of the third or fourth aspect, an StOSt-containing oil/fat is any one or more kinds of transesterification reaction oils obtained by selectively introducing stearic acid into 1,3-positions of an oil/fat in which the 2-position of shea fat, sal fat, allanblackia fat, or a triglyceride is rich in oleic acid.

Advantageous Effects of Invention

By adding and mixing a specific amount of a crystalline S3 component at a temperature that is 0 to 2° C. higher than a cloud point of an SUS-containing oil/fat during a crystallization step, and then performing crystallization, it is possible to improve separability between a crystal fraction and a liquid fraction of an oil/fat, and to obtain a crystal fraction with higher purity. In addition, because an amount of an S3 component added is very small, it is possible to obtain an SUS-rich oil/fat having excellent crystallinity, without impairing the crystallinity of the SUS-rich oil/fat due to an increase in S3 content in the obtained SUS-rich crystal fraction.

DESCRIPTION OF EMBODIMENTS

Hereinafter, a crystallization method in the dry-mode oil/fat separation of the present invention will be described in detail.

Stirring crystallization in the present invention is a step of performing crystallization while stirring a raw material oil/fat melted by heating throughout the time from the start of cooling to the completion of crystallization. In addition, the term "compression filtration" refers to a step of filtering a crystal slurry after crystallization while applying pressure to perform solid-liquid separation, in which a compressed filter cake side is a crystal fraction, and a filtrate side is a liquid fraction.

Typically, the dry-mode oil/fat separation method according to the present invention can be carried out by the following procedure.

1) An SUS-containing oil/fat is heated to 45° C. or higher, preferably 50° C. to 70° C. to be completely liquified.

2) The liquified SUS-containing oil/fat is cooled while stirring in a crystallization tank equipped with a stirrer and a cooling device with a refrigerant.

3) When a temperature of the SUS-containing oil/fat reaches a temperature that is 0 to 2° C. higher than a cloud point of the SUS-containing oil/fat, 5 to 200 ppm of a crystalline S3 component is added, and stirring crystallization is carried out while further cooling the resultant mixture. A temperature of the refrigerant at this time is appropriately set such that the resultant mixture becomes a fluid crystal slurry which can be pumped and transported after crystallization.

4) After the crystallization, the crystal slurry is pumped and transported into a compression filter.

5) The crystal slurry is compression-filtered to be separated into an SUS-concentrated crystal fraction and a filtrate fraction.

6) If necessary, the operations from 1) to 4) are repeated to further separate the filtrate fraction of the first stage into a SUS-concentrated crystal fraction of a second stage and a filtrate fraction of the second stage. As above, an SUS-rich oil/fat is separated in multiple stages, and separated fractions can also be mixed and used.

A stirring speed in the stirring crystallization step is not particularly limited until a temperature of the SUS-containing oil/fat rises to a temperature that is about 5° C. higher than a cloud point thereof from the start of cooling. However, a relatively fast speed is advantageous in that cooling efficiency can be improved and a cooling time can be shortened. Until when subjecting a crystallization slurry to compression filtration from when an oil temperature lowers to a temperature that is about 5° C. higher than a cloud point of the SUS-containing oil/fat, it is preferable to perform low-speed stirring within a range where crystals do not settle in order to obtain crystals with a low residual liquid percentage (entrapped) of filtrate components and with high separation efficiency. A stirring device of the present invention is not particularly limited as long as the device can stir crystals to such an extent that the crystals do not settle during crystallization. It is possible to use a stirring device that uses, as an agitation element, a paddle-type or propeller-type stirring blade, or a cooling cylinder itself disclosed in PCT International Publication No. 2007/082766.

Examples of SUS-containing oils/fats used in the present invention include palm oil containing a large amount of POP (P: palmitic acid, O: oleic acid); a palm mid-melting point component; a palm stearin and palm olein; shea fat, sal fat, or allanblackia fat containing a large amount of StOSt (St: stearic acid, O: oleic Acid); and the like. In addition, it is also possible to use a transesterification reaction oil obtained by selectively introducing one or more kinds of palmitic acid, stearic acid, or behenic acid into 1,3-positions of an oil/fat in which the 2-position of a triglyceride is rich in oleic acid or linoleic acid. Among the SUS-containing oils/fats, particularly an oil/fat containing a large amount of StOSt can be suitably used for the dry-mode oil/fat separation in the present invention.

A cloud point of the SUS-containing oil/fat used in the present invention means a temperature at which a sample starts to become cloudy when the sample is cooled. A measurement method is based on a measurement method of an oil/fat standard analysis test method (2.2.7-1996 cloud point) established by the Japan Oil Chemists' Society. In the present invention, it is necessary that the crystalline S3 component is added to and mixed with the SUS-containing oil/fat at 5 to 200 ppm by weight with respect to an amount of the SUS-containing oil/fat at a temperature that is 0 to 2° C. higher than a cloud point of the SUS-containing oil/fat, and stirring crystallization is performed thereon. A case where the crystalline S3 component is added at a temperature lower than the cloud point is not preferable because a viscosity of a crystal slurry after crystallization increases, and therefore pumping and transporting for the compression filtration step becomes difficult to perform, and furthermore, a residual liquid percentage (entrapped) of filtrate components in crystals increases in the compression filtration step, and therefore separation accuracy decreases. On the contrary, in a case where the crystalline S3 component is added at a temperature that is greater than 2° C. higher than the cloud point, a crystallization time becomes excessively long, and a residual liquid percentage (entrapped) of filtrate components in crystals tends to increase in the compression filtration step.

An amount of crystalline S3 component added to the SUS-containing oil/fat is suitably 5 to 200 ppm by weight. In a case where an amount thereof is less than 5 ppm, a crystallization time becomes excessively long, and a residual liquid percentage (entrapped) of filtrate components in crystals tends to increase in the compression filtration step. On the contrary, a case where an amount exceeds 200 ppm by weight is not preferable because a viscosity of a crystal slurry after crystallization increases, and therefore pumping and transporting for the compression filtration step becomes difficult to perform, and furthermore, a residual liquid percentage (entrapped) of filtrate components in crystals tends to increase in the compression filtration step.

The S3 component used in the present invention means a tri-saturated triglyceride having a saturated fatty acid having 16 to 22 carbon atoms as a constituent fatty acid. Examples thereof include PPP, PPSt, PStSt, StStSt, StStA, StAA, StStB, StBB (P: palmitic acid, St: stearic acid, A: arachidic acid, B: behenic acid), and the like. In a case where a palm mid-melting point component rich in POP is obtained from a raw material oil/fat for separation in which an SUS of the SUS-containing oil/fat contains POP such as palm oil as a main component, it is possible to suitably use S3 components such as PPP and PPSt. In a case where an oil/fat rich in StOSt is obtained from a raw material oil/fat in which an SUS contains StOSt such as shea fat, sal fat, or allanblackia fat as a main component, it is preferable to use S3 components such as PStSt, StStSt, StStA, StAA, StStB, or StBB, and such an S3 component can be easily obtained from an extremely hydrogenated oil of an oil/fat that is in a liquid form at room temperature. Examples of oils/fats that are in a liquid form at room temperature include soybean oil, rapeseed oil, corn oil, sunflower oil, safflower oil, a palm oil low-melting-point component, high erucic acid-containing rapeseed oil, and the like. In addition to the oil/fat that is in a liquid form at room temperature, as S3 component, it is also possible to use a StOSt (O: oleic acid)-containing oil/fat such as shea fat, sal fat, and allanblackia fat; extremely hydrogenated oils thereof; or a separated high-melting-point component rich in S3 components.

Examples of methods for adding the crystalline S3 component include the following methods.

(1) A crystalline powder of an S3 component-containing oil/fat, which has been melted and cooled in advance, is added to a portion collected from an SUS-containing oil/fat set at a temperature 0 to 2° C. higher than a cloud point of the SUS-containing oil/fat; the resultant mixture is mixed for 10 to 30 seconds with a mixer or the like and dispersed; the dispersion liquid is added to the original SUS-containing oil/fat; and crystallization is carried out.

(2) 10 to 30 parts by weight of an S3 component-containing oil/fat and 90 to 70 parts by weight of an oil/fat that is in a liquid form at room temperature are mixed, heated to 80° C., and completely melted, thereafter, cooling to 30 to 40° C. is performed slowly while stirring, and therefore a paste-like crystalline S3 component-containing seed is obtained. A temperature of this crystalline S3 component-containing seed is adjusted to a temperature that is 0 to 2° C. higher than a cloud point of an SUS-containing oil/fat, and a crystalline S3 component-containing seed of which a temperature has been adjusted is added to an SUS-containing oil/fat of which a temperature has reached a temperature 0 to 2° C. higher than a cloud point of the SUS-containing oil/fat, and then crystallization is performed.

A preferred crystal amount of a crystal slurry to be subjected to compression filtration of the present invention is 10 to 20% by weight, and is preferably 10 to 15% by weight as a solid fat content. A case where an amount thereof is less than 10% by weight is not efficient because, although separation performance in compression filtration is favorable, a separation yield of a crystal fraction is low. A case where an amount thereof exceeds 20% by weight is not preferable because a viscosity of a crystal slurry increases, and therefore pumping and transporting for the compression filtration step becomes difficult to perform, and furthermore, a residual liquid percentage (entrapped) of filtrate components in crystals increases in the compression filtration step, and therefore separation accuracy decreases. Measurement of a solid fat content can be easily performed with an NMR-pulse sequence using a solid fat measurement device manufactured by Bruker Corporation, and process management thereof is also easy.

If necessary, an SUS-rich crystal fraction obtained in the dry-mode oil/fat separation of the first stage in the present invention can be converted into a fraction from which a high-melting-point component has been removed by raising a temperature thereof and/or partially dissolving it. Depending on a composition of a raw material oil/fat for separation, in a crystal fraction, a content of high-melting-point-components such as a tri-saturated triglyceride and a di-saturated diglyceride increases as an SUS content increases. When this crystal fraction is made into a cocoa-butter substitute fat without removing these high-melting-point-components, tempering workability of chocolate may deteriorate (thickening during tempering) or a sensation of melting chocolate in the mouth may become unpleasant. In order to prevent such problems, it is possible to obtain an SUS-rich fraction from which most of the high-melting-point components have been removed by a method in which a temperature of a compressed cake of a crystal fraction is raised by heating to dissolve oil/fat components having a melting point lower than that of SUS components in the crystal, only the high-melting-point components are allowed to remain as undissolved components, and filtration is performed with a filter press or the like.

The crystallization method of the present invention can be suitably used for SUS-containing oils/fats having an SUS content of 30% by weight or more. In addition, an SUS content of the SUS-rich oil/fat obtained by the present invention is desirably 60% by weight or more. A case in which an SUS content is less than 60% is not preferable because even though the SUS-rich oil/fat can be used as a cocoa-butter substitute fat, there is a problem that chocolate snapping properties and heat-resisting properties are lowered. In order to obtain a cocoa-butter substitute fat having snapping properties and heat-resisting properties comparable to those of cocoa butter, it is desirable that an SUS content be set to 60% by weight or more, more preferably 70% by weight or more, and most preferably 80% by weight.

The crystallization method of the present invention can be suitably used for separation of an StOSt-rich oil/fat from an SUS-containing oil/fat in which an SUS is substantially composed of StOSt (St: stearic acid, O: oleic acid). In the dry-mode oil/fat separation by stirring crystallization of only one stage of an StOSt-containing oil/fat, there is a strong tendency that as an amount of crystals increases, a crystal slurry thickens, and thus solidification occurs. Therefore, separation of a crystal fraction and a filtrate fraction becomes difficult. By separating crystallization and compression filtration of the present invention into multiple stages to perform separation to obtain an SUS, it is possible to efficiently separate an oil/fat-rich StOSt.

The StOSt-containing oil/fat in the present invention is any one or more kinds of transesterification reaction oils obtained by selectively introducing stearic acid into 1,3-positions of an oil/fat in which the 2-position of shea fat, sal fat, allanblackia fat, or a triglyceride is rich in oleic acid. The present invention can be suitably used for separation of these oils/fats. A transesterification reaction oil obtained by selectively introducing a saturated fatty acid into 1,3-positions of an oil/fat in which the 2-position of a triglyceride is rich in oleic acid, is an oil/fat that is transesterified using a 1,3-position-specific lipase, and using, as a substrate, one or more kinds of oils/fats of separated low-melting-point components of a transesterified oil, which are obtained by selectively introducing stearic acid into 1,3-positions of high oleic sunflower oil, high oleic rapeseed oil, tea seed oil, olive oil, palm-oil soft components, or an oil/fat thereof; and stearic acid or a lower alcohol ester thereof such as an ethyl ester.

EXAMPLES

Hereinafter, the present invention will be specifically described with reference to examples. Test results in each example show the following measurement values.

SFC: solid fat content % of crystal slurry.

SFC measurement method: 3±0.3 g of crystal slurry was sampled into a test tube having a length of 180 mm and a diameter of 10 mm and inserted into a probe of an SFC measurement device, "minispec pc 120 SFC measurement device" manufactured by Bruker Corporation as soon as possible, and a crystal slurry SFC was measured with an NMR pulse sequence.

StOSt content, StOO content: high performance liquid chromatography measurement value.

Filtrate residual liquid percentage (%) in crystal fraction=StOO content of crystal fraction/StOO content of filtrate fraction×100

All % are % by weight. From the residual liquid percentage (%), solid-liquid separation performance after crystallization was evaluated according to the following criteria.

Solid-liquid separation performance: residual liquid percentage of less than 24%: very good, 24 to less than 26%: good, 26 to less than 28%: slightly poor, 28% or more: poor.

<Preparation of Transesterified Oil Obtained by Selectively Introducing Stearic Acid into 1,3-Positions of an Oil/Fat in which the 2-Position of a Triglyceride is Rich in Oleic Acid>

Transesterification of ethyl stearate and high oleic sunflower oil produced in Argentina was carried out using a 1,3-position-specific lipase as a catalyst. Thereafter, an ethyl ester was distilled off to be removed, and therefore a transesterified oil A (StOSt content: 40.8%, StOO content: 27.3%, cloud point: 34.5° C.) was obtained.

Example 1

Transesterified Oil A 14 kg was heated to 60° C. to be melted completely, and placed in a crystallization tank with a diameter of 270 mm and a height of 350 mm which is equipped with a refrigerant jacket, and stirring and cooling was performed while circulating a refrigerant at 35° C. in the refrigerant jacket. A stirring blade of paddle type having a width of 260 mm and a height of 260 mm was used. Cooling was performed at a stirring speed at 40 rpm until an oil temperature decreased from 60° C. to 40° C. After the oil temperature dropped to 40° C., the stirring speed was reduced to 12 rpm to perform stirring crystallization.

When the oil temperature decreased from 60° C. to 35° C., 200 ml was collected from the raw material oil/fat for separation, which is transesterified oil A. 0.14 g of commercially available StStSt powder (β-form stable crystal) was added thereto, and weak stirring was carried out for 10 seconds using a juicer mixer. Therefore, a seed dispersion liquid not containing StStSt powder was prepared as a crystalline S3 component. The entire amount of the seed dispersion liquid was added to the original raw material oil/fat for separation, which is transesterified oil A, and stirring crystallization was continued while further circulating the refrigerant at 35° C. The crystallization was completed at the time when a crystallization time reached 42 hours from the start of cooling. A crystalline amount of the crystal slurry after crystallization was 12.0% as SFC and a slurry viscosity was 6,700 cP.

Thereafter, the crystal slurry was transferred to a compression filter by a pump, and pressurization was performed at 2.0 kg/cm²/min up to 30 Kg/cm² in 15 minutes. The same pressure was held for 15 minutes to perform compression filtration. As a compressed crystal fraction, a crystal fraction concentrated to an StOSt content of 72.2% was obtained at a separation yield of 30.2%. A filtrate residual liquid percentage in the crystal fraction was 22.9%, and solid-liquid separation performance was very good.

35° C. is a temperature 0.5° C. higher than a cloud point of the raw material oil/fat for separation.

Example 2

In place of an StStSt powder of Example 1, an extremely hydrogenated oil powder of high erucic acid rapeseed (fatty acid composition: behenic acid 43.1%, arachidic acid 8%, stearic acid 40%, palmitic acid 4%) was used as an S3 component-containing oil/fat. The powder is a β-form crystal powder prepared by completely melting the extremely hydrogenated oil powder of high erucic acid rapeseed at 80° C., thereafter, holding the melted resultant in a temperature-controlled chamber at 60° C. for 1 week, thereafter, solidifying the same at room temperature, and then finely powderizing in a mortar. In the same manner as in Example 1, a seed dispersion liquid was added to perform stirring crystallization, and crystallization was completed when the time reached a total of 43 hours of crystallization. A crystalline amount of the crystal slurry after the completion of crystallization was 12.8% as SFC and a slurry viscosity was 7,200 cP. When compression filtration was performed in the same manner as in Example 1, as a compressed crystal fraction, a crystal fraction concentrated to an StOSt content of 71.6% was obtained at a separation yield of 32.3%. A filtrate residual liquid percentage in the crystal fraction was 23.8%, and solid-liquid separation performance was very good.

Example 3

In place of the StStSt powder of Example 1, the extremely hydrogenated oil powder of high erucic acid rapeseed described in Example 2 was used. 20 parts of the extremely hydrogenated oil powder of high erucic acid rapeseed and 80 parts of high oleic sunflower oil were mixed and heated to 80° C. to be completely melted. Thereafter, cooling was carried out for 24 hours while gradually stirring the melted resultant in a temperature-controlled chamber at 35° C. Therefore, a paste-like seed dispersion liquid was obtained as a crystalline S3 component. In the same manner as in Example 1, 3.75 g of the seed dispersion liquid was added to the raw material oil/fat for separation to perform stirring crystallization, and crystallization was completed when the time reached a total of 42 hours of crystallization. A crystalline amount of the crystal slurry after the completion of crystallization was 13.0% as SFC and a slurry viscosity was 7,200 cP. When compression filtration was performed in the same manner as in Example 1, as a compressed crystal fraction, a crystal fraction concentrated to an StOSt content of 72.0% was obtained at a separation yield of 31.6%. A filtrate residual liquid percentage in the crystal fraction was 23.2%, and solid-liquid separation performance was very good. A crystalline form of the extremely hydrogenated oil powder of high erucic acid rapeseed in the seed dispersion liquid was an α-form.

crystalline form is a mixture of β and β', DG: diglyceride) was used. In the same manner as in Example 1, a seed dispersion liquid was added to perform stirring crystallization, and crystallization was completed when the time reached a total of 44 hours of crystallization. A crystalline amount of the crystal slurry after the completion of crystallization was 12.4% as SFC and a slurry viscosity was 6,200 cP. When compression filtration was performed in the same manner as in Example 1, as a compressed crystal fraction, a crystal fraction concentrated to an StOSt content of 70.5% was obtained at a separation yield of 32.0%. A filtrate residual liquid percentage in the crystal fraction was 26.8%, and solid-liquid separation performance was slightly poor.

Comparative Example 2

Crystallization was carried out under the following conditions without using a seed agent. In order to precipitate a high-melting-point component at an oil temperature of 60° C., stirring and cooling was performed at a stirring rate of 12 rpm until the temperature lowered to 25° C. while circulating cooling water at 25° C. After the temperature lowered to 25° C., a stirring speed was reduced to 10 rpm. Thereafter, after holding for 80 minutes, cooling water at 35° C. was circulated for reheating to 35° C. Thereafter, stirring crystallization was performed at a stirring speed of 12 rpm at the same temperature, and crystallization was completed when the time reached a total of 51.5 hours of crystallization. A crystalline amount of the crystal slurry after the completion of crystallization was 7.8% as SFC and a slurry viscosity was 6,100 cP.

Thereafter, the crystal slurry was transferred to a compression filter by a pump while maintaining the crystal slurry. Compression filtration was performed in the same manner as in Example 1, and as a crystal fraction, a crystal fraction concentrated to an StOSt content of 69.5% was obtained at a separation yield of 22.2%. A filtrate residual liquid percentage in the crystal fraction was 29.5%, and solid-liquid separation performance was poor.

Table 1 shows the test results of Examples 1 to 3 and Comparative Examples 1 and 2.

TABLE 1

| | | Amount added | Crystal fraction | | | Residual liquid | Filtrate fraction | |
| --- | --- | --- | --- | --- | --- | --- | --- | --- |
| | Seed agent | ppm | Yield % | StOSt % | StOO % | percentage % | StOSt % | StOO % |
| Raw material for separation | — | — | — | 40.8 | 27.3 | — | — | — |
| Example 1 | StStSt | 10 | 30.2 | 72.2 | 8.2 | 22.9 | 27.2 | 35.7 |
| Example 2 | *HER (β-form) | 10 | 32.3 | 71.6 | 8.7 | 23.8 | 26.2 | 36.6 |
| Example 3 | *HER (α-form) | 10 | 31.6 | 72.0 | 8.4 | 23.2 | 26.4 | 36.1 |
| Comparative Example 1 | StSt-DG | 10 | 32.0 | 70.5 | 9.3 | 26.8 | 26.8 | 35.4 |
| Comparative Example 2 | Not added | Not added | 22.2 | 69.5 | 9.6 | 29.5 | 32.6 | 32.4 |

*HER: extremely hydrogenated oil of high erucic acid rapeseed

Comparative Example 1

In place of the StStSt powder of Example 1, an StSt-DG powder (a reagent, a mixture of 1,2-DG and 1,3-DG, a In Examples 1 to 3 in which 10 ppm of an StStSt powder or an extremely hydrogenated oil powder of high erucic acid rapeseed was added as a crystalline S3 component, a crystal fraction having a low filtrate residual liquid percentage was obtained, and solid-liquid separation performance was very good, when compared with Comparative Example 1 in which StSt-DG was used as a seed agent and Comparative Example 2 in which no seed agent was added. In Comparative Example 1 and Comparative Example 2, a filtrate residual liquid percentage tended to be slightly higher, and solid-liquid separation performance was slightly poor or poor.

Example 4

A seed dispersion liquid containing a crystalline S3 component was obtained in the same manner as in Example 1, except that an amount of StStSt powder added in Example 1 was changed from 0.14 g to 1.4 g. In the same manner as in Example 1, a seed dispersion liquid was added to perform stirring crystallization, and crystallization was completed when the time reached a total of 48 hours of crystallization. A crystalline amount of the crystal slurry after the completion of crystallization was 12.7% as SFC and a slurry viscosity was 8,200 cP. When compression filtration was performed in the same manner as in Example 1, as a compressed crystal fraction, a crystal fraction concentrated to an StOSt content of 71.4% was obtained at a separation yield of 32.7%. A filtrate residual liquid percentage in the crystal fraction was 23.4%, and solid-liquid separation performance was very good.

Example 5

A seed dispersion liquid containing a crystalline S3 component was obtained in the same manner as in Example 1, except that an amount of StStSt powder added in Example 1 was changed from 0.14 g to 2.8 g. In the same manner as in Example 1, a seed dispersion liquid was added to perform stirring crystallization, and crystallization was completed when the time reached a total of 48 hours of crystallization. A crystalline amount of the crystal slurry after the completion of crystallization was 14.4% as SFC and a slurry viscosity was 12,200 cP. When compression filtration was performed in the same manner as in Example 1, as a compressed crystal fraction, a crystal fraction concentrated to an StOSt content of 70.9% was obtained at a separation yield of 34.9%. A filtrate residual liquid percentage in the crystal fraction was 24.9%, and solid-liquid separation performance was good.

Example 6

A seed dispersion liquid containing a crystalline S3 component was obtained in the same manner as in Example 1, except that an amount of extremely hydrogenated oil powder of high erucic acid rapeseed added in Example 2 was changed from 0.14 g to 1.4 g. In the same manner as in Example 1, a seed dispersion liquid was added to perform stirring crystallization, and crystallization was completed when the time reached a total of 43 hours of crystallization. A crystalline amount of the crystal slurry after the completion of crystallization was 12.0% as SFC and a slurry viscosity was 7,200 cP. When compression filtration was performed in the same manner as in Example 1, as a compressed crystal fraction, a crystal fraction concentrated to an StOSt content of 70.6% was obtained at a separation yield of 32.7%. A filtrate residual liquid percentage in the crystal fraction was 25.1%, and solid-liquid separation performance was good.

Comparative Example 3

A seed dispersion liquid containing a crystalline S3 component was obtained in the same manner as in Example 1, except that an amount of StStSt powder added was changed from 0.14 g to 3.5 g in Example 1. In the same manner as in Example 1, a seed dispersion liquid was added to perform stirring crystallization, and crystallization was completed when the time reached a total of 40 hours of crystallization. A crystalline amount of the crystal slurry after the completion of crystallization was 14.0% as SFC and a slurry viscosity was 7,600 cP. When compression filtration was performed in the same manner as in Example 1, as a compressed crystal fraction, a crystal fraction concentrated to an StOSt content of 69.7% was obtained at a separation yield of 36.6%. A filtrate residual liquid percentage in the crystal fraction was 27.0%, and solid-liquid separation performance was slightly poor.

Comparative Example 4

A seed dispersion liquid was obtained in the same manner as in Example 4 using 1.4 g of stable crystal flakes of StOSt (flakes obtained by thinly grinding a surface of Melano SS400 filled in a case manufactured by FUJI OIL CO., LTD.) in place of 1.4 g of an StStSt powder of Example 4. In the same manner as in Example 1, a seed dispersion liquid was added to perform stirring crystallization, and crystallization was completed when the time reached a total of 26 hours of crystallization. A crystalline amount of the crystal slurry after the completion of crystallization was 7.9% as SFC and a slurry viscosity was 5,800 cP. Compression filtration was attempted in the same manner as Example 1, but a viscosity of the crystal slurry after the crystallization rapidly increased, thereby resulting in a state in which compression filtration was not able to be performed.

Table 2 shows the test results of Examples 4 to 6 and Comparative Examples 3 and 4.

TABLE 2

| | | | | Crystal fraction | | | Filtrate fraction | |
| | | | | | | Residual liquid | | |
| | | Amount | | | | | | |
| | Seed agent | added ppm | Yield % | StOSt % | StOO % | percentage % | StOSt % | StOO % |
| --- | --- | --- | --- | --- | --- | --- | --- | --- |
| Raw material for separation | — | — | — | 40.8 | 27.3 | — | — | — |
| Example 4 | StStSt | 100 | 32.7 | 71.4 | 8.4 | 23.4 | 25.9 | 36.0 |
| Example 5 | StStSt | 200 | 34.9 | 70.9 | 9.2 | 24.9 | 24.8 | 37.0 |
| Example 6 | * HER (β-form) | 100 | 32.7 | 70.6 | 8.9 | 25.1 | 26.4 | 35.7 |

TABLE 2-continued

| | | Amount | Crystal fraction | | | Residual liquid | Filtrate fraction | |
|---|---|---|---|---|---|---|---|---|
| | Seed agent | added ppm | Yield % | StOSt % | StOO % | percentage % | StOSt % | StOO % |
| Comparative Example 3 | StStSt | 250 | 36.6 | 69.7 | 9.8 | 27.0 | 24.1 | 37.6 |
| Comparative Example 4 | StOSt (β-form) | 100 | Compression filtration is not possible because of viscosity | | | | | |

* HER: extremely hydrogenated oil of high erucic acid rapeseed

In Examples 4 to 6 in which 100 ppm or 200 ppm of an StStSt powder or extremely hydrogenated oil powder of high erucic acid rapeseed was added as seeding agent containing a crystalline S3 component, a crystal fraction having a relatively low filtrate residual liquid percentage was obtained, and solid-liquid separation performance was good. In Comparative Example 3 in which 250 ppm of an StStSt powder was added as a seed agent containing a crystalline S3 component, a filtrate residual liquid percentage tended to be slightly high, and solid-liquid separation performance slightly poor. In addition, in Comparative Example 4 in which stable crystal flakes of StOSt were used as a seed agent, a viscosity of slurry greatly increased due to a rapid increase in an amount of crystals after the completion of crystallization, and therefore the crystal slurry could not be subjected to compression filtration.

Example 7

A temperature for preparing the seed dispersion liquid containing a crystalline S3 component, and a temperature for adding the seed dispersion liquid of Example 1, which were 35° C., were changed to 36° C. for both cases. Stirring crystallization was performed at 36° C. for 10 hours in total. Thereafter, the temperature was cooled to 35° C. and stirring crystallization was performed at 35° C. for a total of 38 hours. A crystalline amount of the crystal slurry after the completion of crystallization was 10.8% as SFC and a slurry viscosity was 5,700 cP. When compression filtration was performed in the same manner as in Example 1, as a compressed crystal fraction, a crystal fraction concentrated to an StOSt content of 72.0% was obtained at a separation yield of 28.3%. A filtrate residual liquid percentage in the crystal fraction was 23.9%, and solid-liquid separation performance was very good. 36° C. is a temperature 1.5° C. higher than a cloud point of the raw material oil/fat for separation.

Comparative Example 5

A temperature for preparing the seed dispersion liquid containing a crystalline S3 component, and a temperature for adding the seed dispersion liquid of Example 1, which were 35° C., were changed to 34° C. for both cases. Stirring crystallization was performed at 34° C. for 10 hours in total. Thereafter, the temperature was cooled to 35° C. and stirring crystallization was performed at 35° C. for a total of 38 hours. A crystalline amount of the crystal slurry after the completion of crystallization was 15.0% as SFC and a slurry viscosity was 8,000 cP. When compression filtration was performed in the same manner as in Example 1, as a compressed crystal fraction, a crystal fraction concentrated to an StOSt content of 69.0% was obtained at a separation yield of 36.0%. A filtrate residual liquid percentage in the crystal fraction was 28.5%, and solid-liquid separation performance was poor. 34° C. is a temperature 0.5° C. lower than a cloud point of the raw material oil/fat for separation.

Comparative Example 6

A temperature for preparing the seed dispersion liquid containing a crystalline S3 component, and a temperature for adding the seed dispersion liquid of Example 1, which were 35° C., were changed to 37° C. for both cases. Stirring crystallization was performed at 37° C. for 10 hours in total. Thereafter, the temperature was cooled to 35° C. and stirring crystallization was performed at 35° C. for a total of 38 hours. A crystalline amount of the crystal slurry after the completion of crystallization was 10.0% as SFC and a slurry viscosity was 6,000 cP. When compression filtration was performed in the same manner as in Example 1, as a compressed crystal fraction, a crystal fraction concentrated to an StOSt content of 69.0% was obtained at a separation yield of 23.0%. A filtrate residual liquid percentage in the crystal fraction was 30.0%, and solid-liquid separation performance was poor. 37° C. is a temperature 2.5° C. higher than a cloud point of the raw material oil/fat for separation.

Table 3 shows the test results of Examples 1 and 7 and Comparative Examples 5 and 6.

TABLE 3

| | Temperature for adding seed agent | Amount added ppm | Crystal fraction | | | Residual liquid percentage % | Filtrate fraction | |
|---|---|---|---|---|---|---|---|---|
| | | | Yield % | StOSt % | StOO % | | StOSt % | StOO % |
| Raw material for separation | — | — | — | 40.8 | 27.3 | — | — | — |
| Example 1 | Cloud point +0.5° C. | 10 | 30.2 | 72.2 | 8.2 | 22.9 | 27.2 | 35.7 |

TABLE 3-continued

|  | Temperature for adding seed agent | Amount added ppm | Crystal fraction | | | | Filtrate fraction | |
|---|---|---|---|---|---|---|---|---|
|  |  |  | Yield % | StOSt % | StOO % | Residual liquid percentage % | StOSt % | StOO % |
| Example 7 | Cloud point +1.5° C. | 10 | 28.3 | 72.0 | 8.3 | 23.9 | 28.6 | 34.9 |
| Comparative Example 5 | Cloud point −0.5° C. | 10 | 36.0 | 69.0 | 10.0 | 28.5 | 24.9 | 37.0 |
| Comparative Example 6 | Cloud point +2.5° C. | 10 | 23.0 | 69.0 | 9.7 | 30.0 | 32.4 | 32.6 |

In Examples 1 and 7 in which 10 ppm of an StStSt powder was added as a seeding agent containing a crystalline S3 component at temperatures that are 0.5° C. and 1.5° C. higher than a cloud point of the raw material oil/fat for separation, a crystal fraction with a low filtrate residual liquid percentage was obtained, and solid-liquid separation performance was very good. In Comparative Example 5 in which the seed dispersion liquid was added at a temperature that is 0.5° C. lower than a cloud point of the raw material oil/fat for separation, and in Comparative Example 6 in which the seed dispersion liquid was added at a temperature that is 2.5° C. higher than a cloud point of the raw material oil/fat for separation, a filtrate residual liquid percentage tended to be high, and solid-liquid separation performance was poor.

INDUSTRIAL APPLICABILITY

The present invention relates to a crystallization method of an oil/fat by stirring crystallization, in which it is possible to improve separability between a crystal fraction and a liquid fraction of an oil/fat, and to obtain a crystal fraction with higher purity in the dry-mode oil/fat separation.

The invention claimed is:

1. A crystallization method, comprising:
adding a crystalline S3 component to an SUS-containing oil/fat at 5 to 200 ppm by weight with respect to an amount of the SUS-containing oil/fat at a temperature that is 0 to 2° C. higher than a cloud point of the SUS-containing oil/fat so as to be mixed, and performing stirring crystallization, in dry-mode oil/fat separation for obtaining an SUS-rich oil/fat having an SUS content of 60% by weight or more from the SUS-containing oil/fat having an SUS content of 30% by weight or more by employing stirring crystallization and compression filtration,
wherein SUS is a 1,3-di-saturated-2-unsaturated glyceride, S3 is a tri-saturated triglyceride, S of each of SUS and S3 is a saturated fatty acid having 16 to 22 carbon atoms, and U of SUS is an unsaturated fatty acid having 18 carbon atoms.

2. The crystallization method according to claim 1, wherein a crystalline amount of a crystal slurry subjected to the compression filtration is 10 to 20% by weight as a solid fat content.

3. The crystallization method according to claim 2, wherein the SUS is StOSt, St of StOSt is a stearic acid, and O of StOSt is an oleic acid.

4. The crystallization method according to claim 3, wherein the S3 component is a tri-saturated triglyceride derived from an extremely hydrogenated oil of an oil/fat that is in a liquid form at room temperature.

5. The crystallization method according to claim 3, wherein an StOSt-containing oil/fat is any one or more kinds of transesterification reaction oils obtained by selectively introducing stearic acid into 1,3-positions of an oil/fat in which the 2-position of shea fat, sal fat, allanblackia fat, or triglyceride is rich in oleic acid.

6. The crystallization method according to claim 4, wherein an StOSt-containing oil/fat is any one or more kinds of transesterification reaction oils obtained by selectively introducing stearic acid into 1,3-positions of an oil/fat in which the 2-position of shea fat, sal fat, allanblackia fat, or triglyceride is rich in oleic acid.

* * * * *